United States Patent [19]
Wennerberg et al.

[11] Patent Number: 5,019,710
[45] Date of Patent: May 28, 1991

[54] OPTICAL SYSTEM FOR DETECTING PROPERTIES OF TRAVELING SHEET MATERIALS

[75] Inventors: Gunnar Wennerberg; Daniel A. Gordon; Harriss T. King, all of Cupertino, Calif.

[73] Assignee: Measurex Corporation, Cupertino, Calif.

[21] Appl. No.: 331,404

[22] Filed: Mar. 30, 1989

[51] Int. Cl.$^5$ ............................................. G01N 21/01
[52] U.S. Cl. ................................. 250/341; 250/359.1
[58] Field of Search .................... 250/341, 340, 259.1, 250/227.11; 356/239

[56] References Cited
U.S. PATENT DOCUMENTS 3,806,730  4/1974  Tirkkonen et al. ................. 250/341
4,343,991  8/1982  Fujiwara et al. ............... 250/227.11
4,515,165  5/1985  Carroll ............................... 250/341

FOREIGN PATENT DOCUMENTS 0129334  8/1983  Japan .................................. 250/341

Primary Examiner—Edward P. Westin
Assistant Examiner—Richard Hanig
Attorney, Agent, or Firm—Burns, Doane, Swecker & Mathis

[57] ABSTRACT

A system for detecting optically-sensitive properties of sheet materials during manufacture includes a first group of bundles of optical fibers that convey light to selected transmitting locations adjacent one face of the sheet material. The system further includes a second group of bundles of optical fibers that collect and convey light transmitted through the sheet material to a light detector. The light detector measures the intensity of light received from each of the bundles of the second group to provide measurements of optically-sensitive properties of the sheet material at selected cross-directional locations.

8 Claims, 4 Drawing Sheets

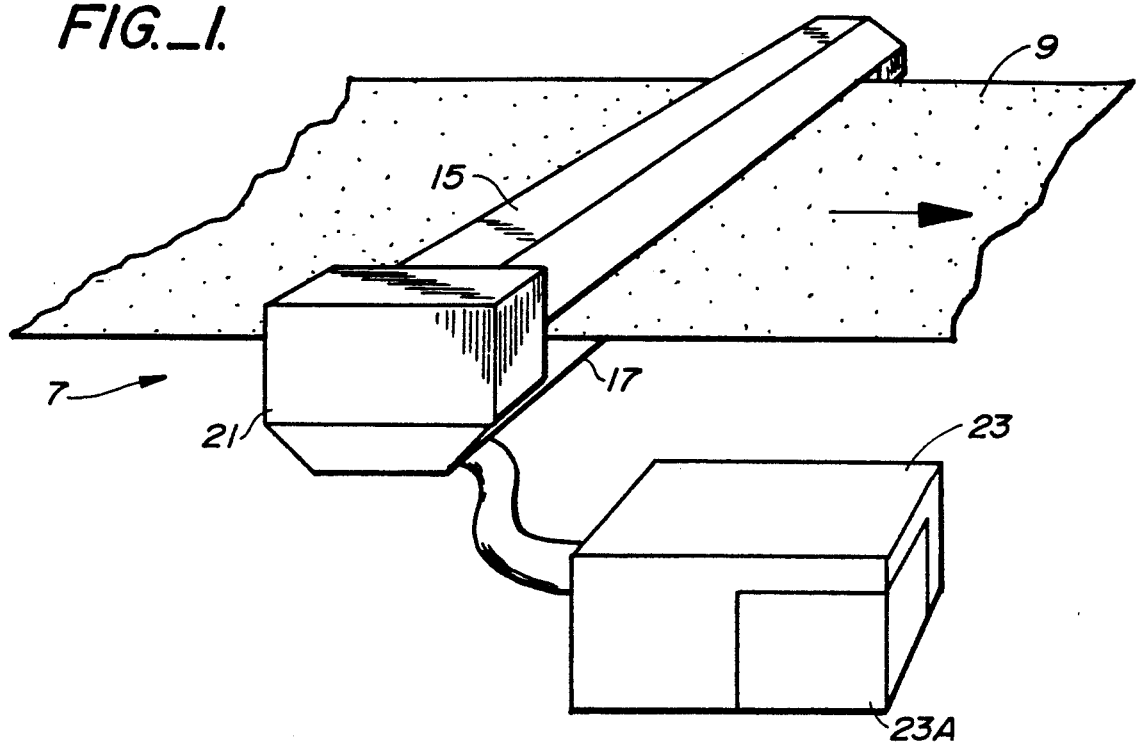
FIG._1.
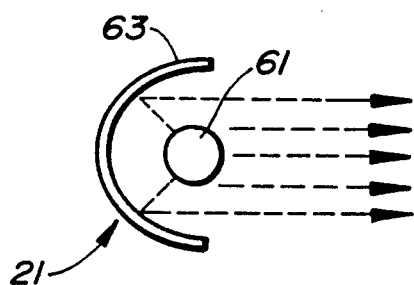
FIG._3.
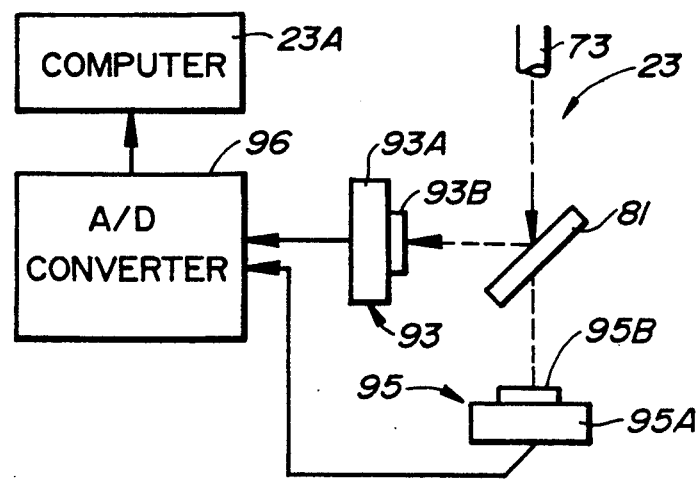
FIG._6.

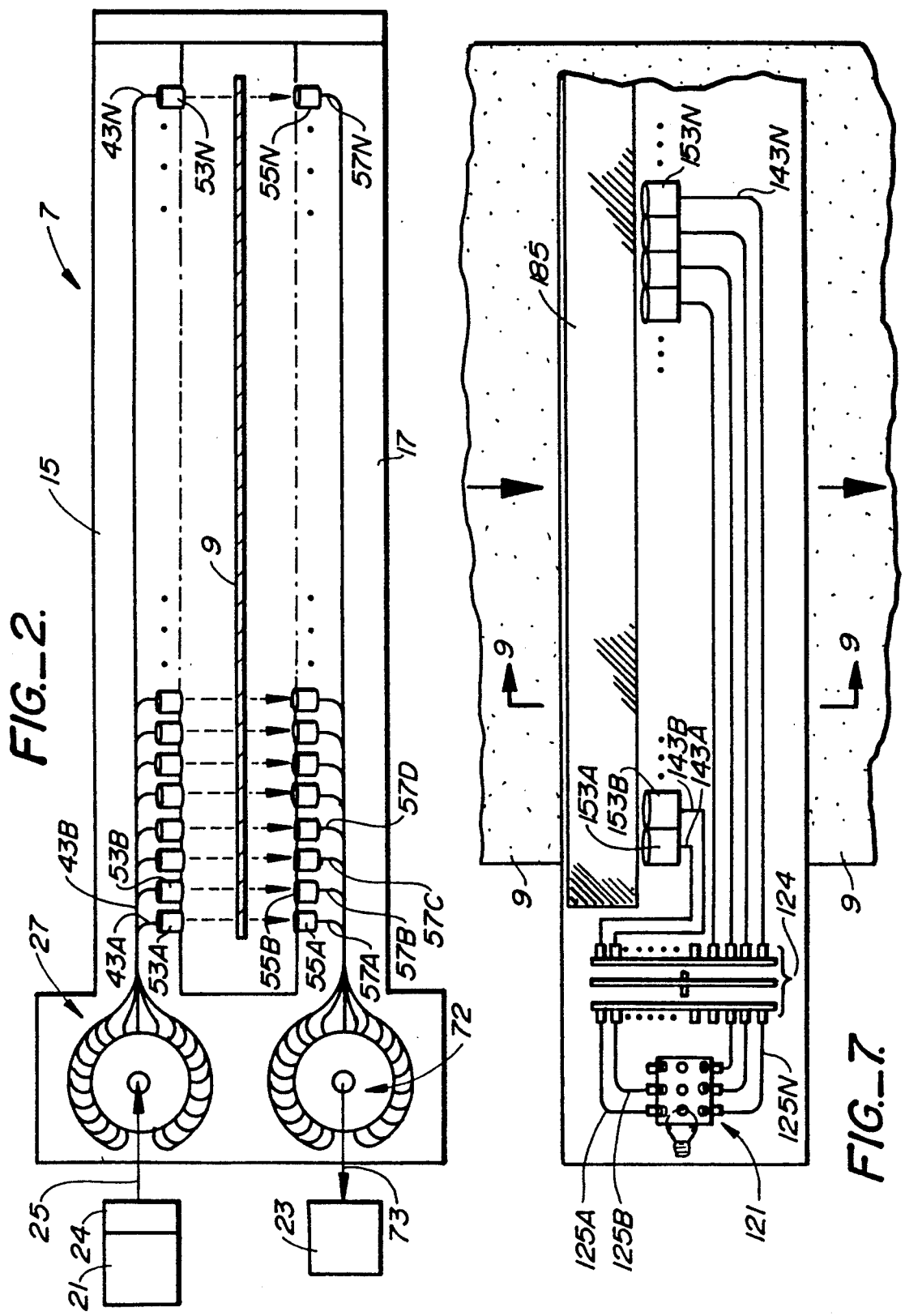

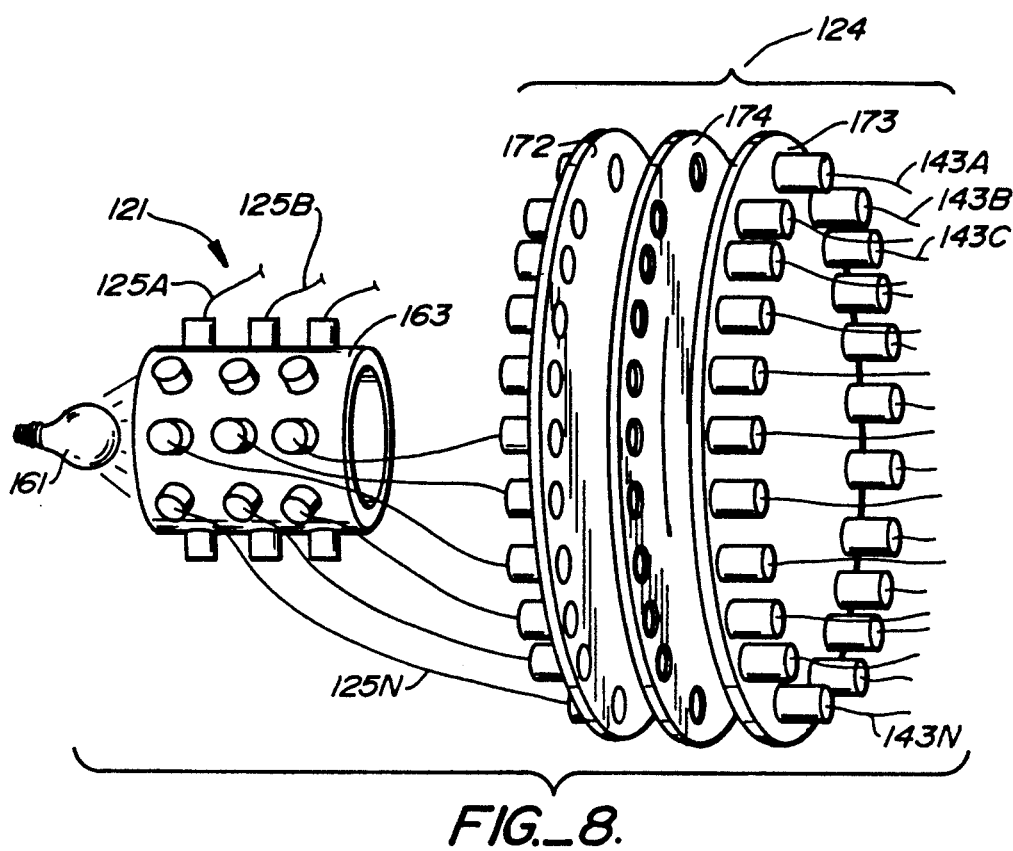
FIG._8.
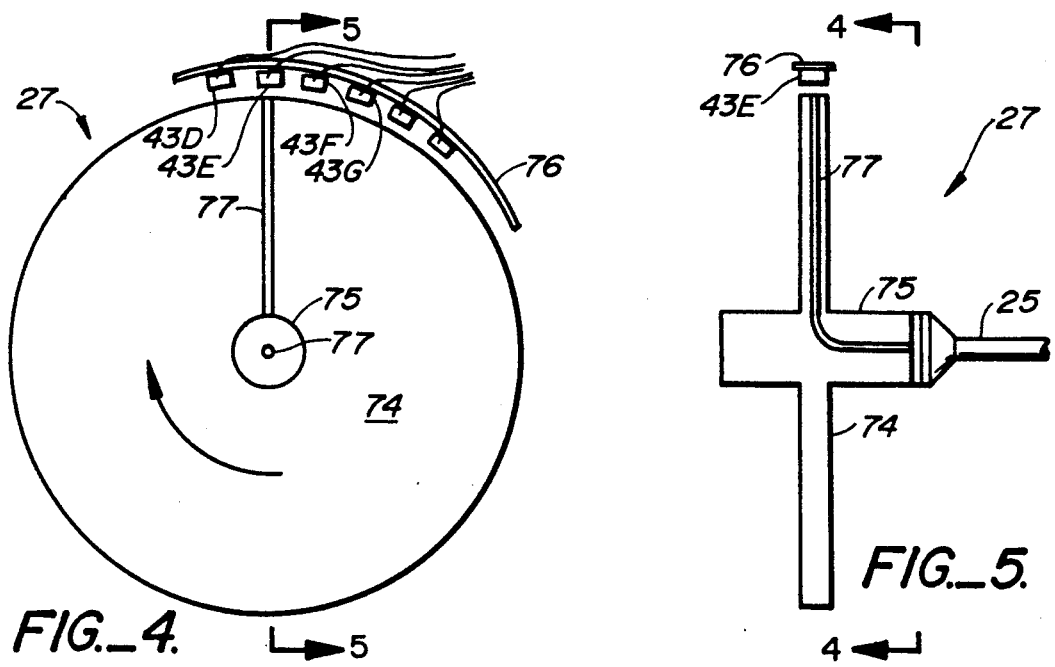
FIG._4.
FIG._5.

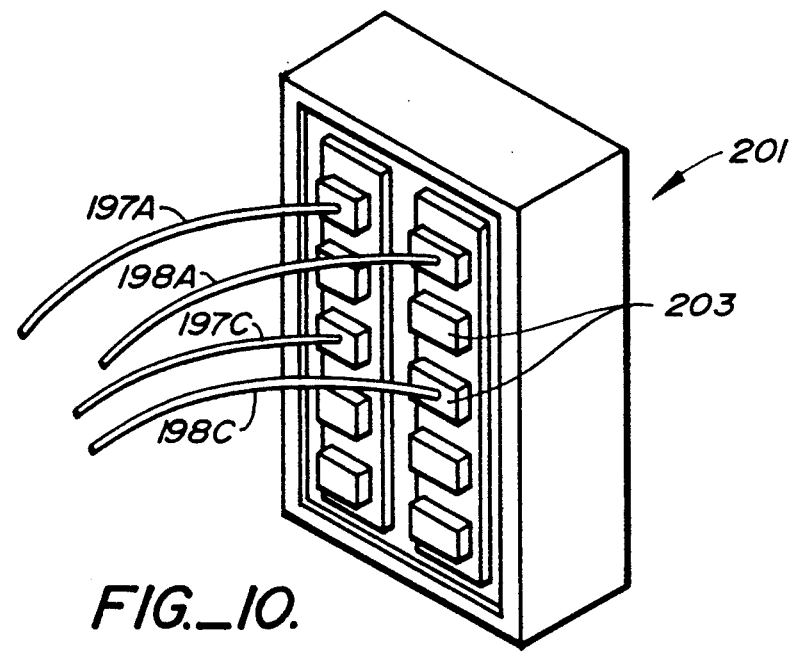
FIG._10.
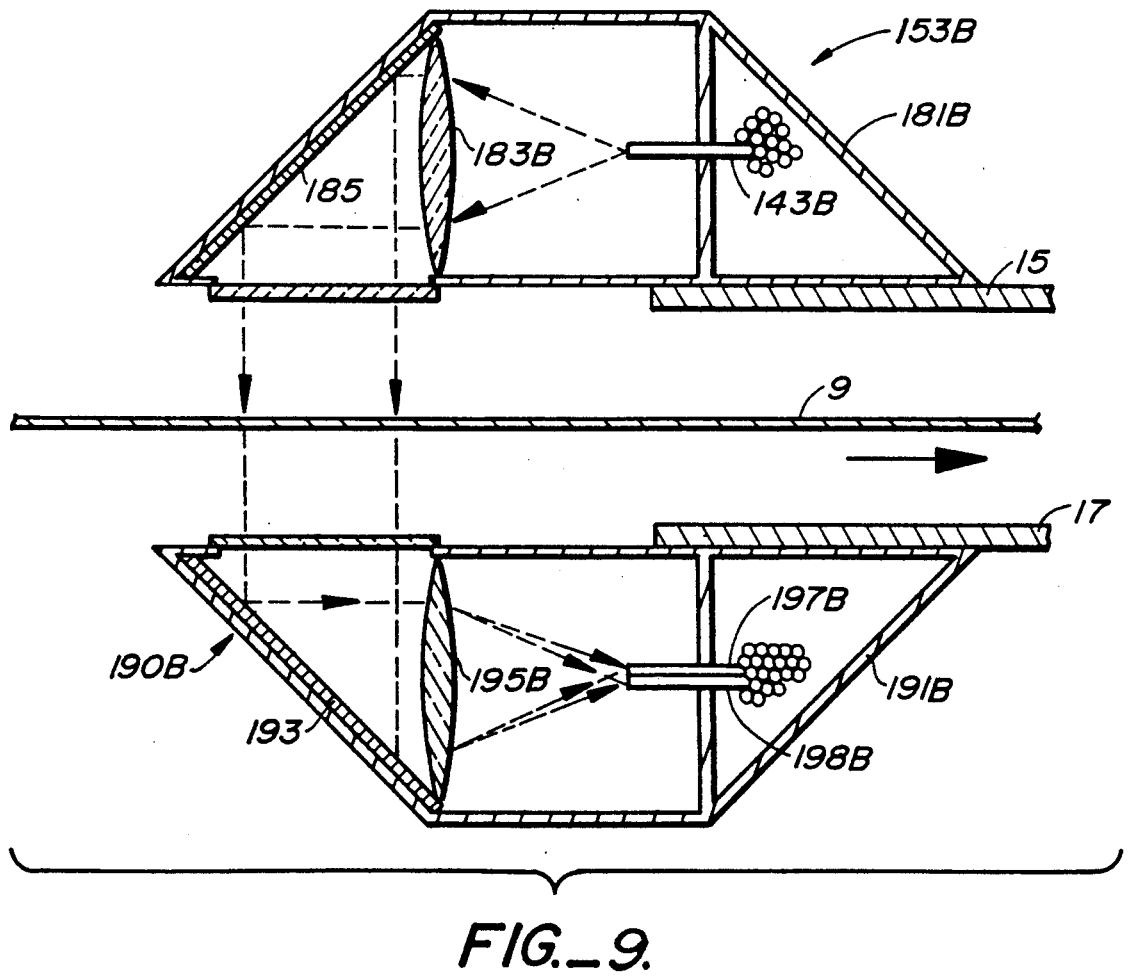
FIG._9.

OPTICAL SYSTEM FOR DETECTING PROPERTIES OF TRAVELING SHEET MATERIALS

TECHNICAL FIELD OF THE INVENTION

The present invention generally relates to systems for measuring properties of sheet materials during manufacture and, more particularly, to measurement systems using optical methods for measuring sheet properties.

BACKGROUND ART

In the manufacture of sheet materials, it is well known that various sheet properties can be detected "on-line,", i.e., while a sheetmaking machine is operating. On-line measurement devices include, for example, ones that measure sheet properties such as basis weight, dry basis weight, moisture content, and thickness. Typically, such on-line devices employ sensors that periodically traverse, or scan, sheets in the cross direction (i.e., in the direction perpendicular to the direction of sheet travel). Depending upon the particular sheetmaking machine, cross-directional distances can range from about 100 inches to over 400 inches.

Known scanning sensors for use on sheetmaking machines include ones that measure basis weight by detecting the amount of radiation that a sheet absorbs from beams of infrared light or other radiation of known wavelength. In systems employing such sensors, radiation through a sheet is usually compared at two different bands of wavelengths, one of which is a measurement wavelength band and the other of which is a reference wavelength band. Although scanning sensors have numerous advantages, they also have some practical shortcomings. For example, the time required to make a cross-directional traverse may cause control delays, sometimes exceeding several minutes.

Because of the limitations of conventional scanning sensors, it has been proposed to mount a plurality of identical sensors at fixed cross-directional locations on sheetmaking machines to detect sheet properties. For example, U.S. Pat. No. 3,806,730 suggests that an on-line measuring system can include a set of stationary distributor tubes that distribute light from a single source onto the surface of a travelling sheet. According to the patent, the distributor tubes are aluminum pipes that have reflective interior surfaces. The system described in the patent further includes a similar set of receiver tubes which are mounted to receive and convey light which has been transmitted through the sheet. The receiver tubes carry the received light to detectors whose outputs, according to the patent, can be used for estimating the basis weight and moisture content of sheet material. The patent teaches that each distributor tube is associated with a particular receiver tube so that, for any pair of tubes, the total light transmission distance is the same. Accordingly, from a practical standpoint, the system in U.S. Pat. No. 3,806,730 requires that the light source and detector are situated at opposite edges of a sheet.

SUMMARY OF THE INVENTION

Generally speaking, the present invention provides a system for measuring optically sensitive properties of sheet materials without traveling sensors. The measured properties can include, for example, dry basis weight and moisture. More particularly, a system according to the present invention generally comprises a first group of bundles of optical fibers which are connected to convey infrared light from a light source to stations whereat the light is directed onto one face of a sheet of material at generally regularly-spaced locations. Further, the system includes a second group of bundles of optical fibers which are connected to convey light which has been transmitted through the sheet material. Still further, the system includes a light detector connected to the optical fibers of the second group to provide measurements of optically sensitive properties of the sheet material.

BRIEF DESCRIPTION OF THE DRAWINGS

The foregoing and other aspects of the present invention can be readily ascertained by reference to the following description and attached drawings which illustrate preferred embodiments of the present invention. In the various drawing figures, like elements are given the same reference numerals.

In the drawings:

FIG. 1 is a highly generalized diagram of a measurement system according to the present invention;

FIG. 2 is a vertical cross-sectional view showing one embodiment of the components of the measurement system of FIG. 1;

FIG. 3 is a schematic diagram of one embodiment of a light source for use with the measurement system of FIG. 2

FIG. 4 is a frontal view of one embodiment of an optical multiplexor for use with the measurement system of FIG. 2;

FIG. 5 is a cross-sectional view of the optical multiplexor of FIG. 4 taken along the plane of the line 5—5 for viewing in the direction of the arrows;

FIG. 6 is a functional diagram of a light detection system for use with the measurement system of FIG. 2;

FIG. 7 is a top plan view, partially cut away, of an alternative embodiment of the measurement system of FIG. 1;

FIG. 8 is a pictorial view of one embodiment of an optical multiplexor for use with the measurement system of FIG. 7;

FIG. 9 is a cross-sectional view of light transmission and receiver stations for use with the measurement system of FIG. 7; and FIG. 10 is a schematic diagram of a light detector array for use with the measurement system of FIG. 7.

DETAILED DESCRIPTION OF THE PREFERRED EMBODIMENT AND BEST MODE OF CARRYING OUT THE INVENTION

FIG. 1 generally shows a measurement system for mounting on a sheetmaking machine to provide optical measurements of sheet material 9 being produced by the machine. The sheet material can be, for example, plastic or paper. The measured property of the sheet material normally is basis weight or moisture content. The direction of travel of sheet material 9 is indicated by the arrow.

In structural terms, the measurement system of FIG. 1 includes parallel members 15 and 17 which are mounted to horizontally spa the sheetmaking machine adjacent the opposite faces of sheet 9. As will be described in further detail below, the measurement system generally includes a light source 21 for transmitting modulated light to selected stations 53A–53N which are located along member 15 for focusing the light onto the adjacent surface of sheet 9. Receiver stations, not shown in FIG. 1, collect light which has passed through sheet 9 and convey the collected light to a detector 23. The output of detector 23 is conveyed to a conventional microprocessor-based computer 23A for calculation of the properties of sheet 9 at selected cross-directional locations. In practice, detector 23 and computer 23A can be located at virtually any convenient location, including locations which are substantially remote from the sheetmaking machine.

Two specific embodiments of the measuring system of FIG. 1 will now be described. The first embodiment is shown in FIGS. 2 through 6, and the second embodiment is shown in FIGS. 7 through 11. Although both embodiments have the same general exterior appearance, many of their components are different.

In the system in FIG. 2, light source 21 is connected to a modulating device 24 which comprises, for example, a shutter-type mechanism that repetitively produces pulses of the source light. As also shown in FIG. 2, a fiber-optic bundle 25 is mounted to carry light from modulating device 24 to a first rotary multiplexor 27. From rotary multiplexor 27, fiber-optic bundles 43A–43N of various lengths extend to transmitter stations 53A–53N. More particularly, fiber-optic bundle 43A is connected to transmitter station 53A, fiber-optic bundle 43B is connected to transmitter station 53B, and so forth. Each of the transmitter stations 53A–53N is stationarily mounted on structural member 15 and is positioned to direct light generally perpendicularly onto the surface of sheet 9, as indicated by the vertical arrows in FIG. 2.

As also shown in FIG. 2, receiver stations 55A–55N are stationarily mounted along structural member 17 in vertical alignment with respective ones of the transmitter stations 53A–53N. From the receiver stations 55A–55N, respectively, fiber-optic bundles 57A–57N carry the received light to a second rotary multiplexor 72. From second rotary multiplexor 72, light is transmitted to detector 23 via a fiber-optic bundle 73.

One embodiment of light source 21 is shown in FIG. 3. In this embodiment, the light source comprises an incandescent lamp 61 mounted stationarily within the area encompassed by parabolic reflector 63. In practice, lamp 61 is of the type which emits a broad spectrum of infrared radiation including light within the wavelength band between 1.3 and 2.1 microns.

One embodiment of rotary multiplexor 2 is shown in FIGS. 4 and 5. In this embodiment, the rotary multiplexor includes a rotable disc 74 which has an aperture 75 formed along its central axis. Extending from aperture 75 to the periphery of disc 74 is a fiber-optic bundle 77. In practice, fiber-optic bundle 77 is mounted to rotate with the disc. Rotary multiplexor 27 also includes a stationary rim member 76 which is mounted to surround the periphery of disc 74. The rim member 76 provides a mounting means for fiber-optic bundles 43A–43N which, in the illustrated embodiment, attach to the rim member at spaced-apart locations such that the ends of the bundles are directed toward the periphery of disc 74.

The operation of rotary multiplexor 27 of FIGS. 4 and 5 will now be described. In operation, disc 74 is driven to rotate at a generally constant speed while pulsed light is conveyed from strand 25 to strand 77. (FIG. 5 shows the optical connection between fiber-optic strands 25 and 77.) As disc 74 rotates, fiber-optic bundle 77 sequentially transmits light to bundles 43A–43N. For example, with disc 74 in the position shown in FIG. 4, the outward end of fiber-optic bundle 77 is in optical communication with the end of fiber-optic bundle 43E. Then, as disc 74 rotates clockwise from the position shown in FIG. 4, bundle 77 will sequentially distribute light to bundles 43F, 43G, and so forth.

It should be understood that the second rotary multiplexor 72 (FIG. 1) can be structurally identical to multiplexor 27. In operation, second rotary multiplexor 72 receives pulses of light sequentially from fiber-optic bundles 57A–57N and then transmits the received pulses, in series, along bundle 73 in series. Multiplexors 27 and 72 can be operated synchronously.

FIG. 6 shows one example of components comprising light detector 23. In this embodiment, light detector 23 includes a beam-splitting mirror 81 which is arranged at the end fiber-optic bundle 73, a first photoelectric detector 93 which is mounted to receive reflected rays from beam-splitting mirror 81, and a second photoelectric detector 95 which is mounted to receive transmitted rays. The detector 23 further includes a conventional analog-to-digital converter 96 which is connected to receive output signals from photoelectric detectors 93 and 95. In practice, photoelectric detectors 93 and 95 each includes an optical bandpass filter and a photoelectric transducer. Thus, in FIG. 6, the bandpass filter associated with detector 93 is designated 93B and the photoelectric associated with detector 93 is designated 93A. Similarly, the bandpass filter associated with detector 95 is designated 95B and the photoelectric transducer associated with that detector is designated 95A.

In the light detector of FIG. 6, bandpass filters 93B and 95B normally differ from each other in terms of the wavelengths of light which they pass. For convenience of discussion, the wavelengths of light passed by bandpass filter 93B will be called "measurement" wavelengths and the wavelengths passed by bandpass filter 95B will be called the "reference" wavelengths. When measurements are made in paper-making operations, for example, the measurement wavelengths normally are selected for preferential absorption by paper and the reference wavelengths are selected for less substantial absorption In operation of light detector 23 of FIG. 6, photoelectric transducers 93A and 95A provide analog signals to analog-to-digital converter 96. Then, converter 96 digitizes the analog signals and conveys the digital signals to computer 23A. Based upon the digital signals and conventional algorithms, computer 23A calculates numerical values representing a measure of a property of web 9 for each cross-directional location at which measurements are taken.

Operation of the complete measurement system of FIGS. 2–6 will now be described. To initiate operation, light source 21 is activated and modulating device 24 is operated. Typically, modulating device 24 chops light at a relatively high frequency, say above 525 hertz. The chopped light is conveyed, via fiber-optic bundle 25, to rotary multiplexor 27. As described above, multiplexor 27 operates to sequentially distribute the chopped light to fiber-optic bundles 43A–43N. The bundles 43A–43N carry the distributed light to respective transmitter stations 53A–53N which function to direct the light generally perpendicularly onto the adjacent surface of sheet 9. The light which passes through the sheet is collected at receiver stations 55A–55N and then conveyed to second rotary multiplexor 72 via fiber-optic bundles 57A-57N, respectively. From multiplexor 72, the light is carried to detector 23 via fiber-optic bundle 73. At detector 23, the light is processed, as described above, to provide measurements of the selected property of sheet 9 at the various cross-directional measurement locations.

FIG. 7 shows an alternative embodiment of the measurement system of FIG. 1. The embodiment in FIG. 7 includes a light source 121 and a device 124 for distributing light to transmitter stations 143A-143N which are stationarily mounted at spaced-apart locations to span sheet 9. In particular, light source 121 is connected to light distributor 124 by fiber-optic bundles 125A-125N of various lengths. In turn, light distributor 124 is connected to transmitter stations 153A-153N via fiber-optic bundles 143A-143N, respectively.

Light source 121 is particularly shown in FIG. 8. In this embodiment, light source 121 includes a lamp 161 mounted within a hollow cylindrical member 163. The sidewall of cylindrical member 163 is perforated by apertures, and the ends of fiber-optic bundles 164A-164N are mounted within the apertures so that the bundles receive light from lamp 161.

FIG. 8 also shows a particular embodiment of light distributor 124. In the illustrated embodiment, light distributor 124 comprises two mounting members 172 and 173 separated by a rotatable disc member 174. The first mounting member 172 includes a circular array of regularly-spaced apertures which receive the ends of fiber-optic bundles 125A-125N. An identical circular array of regularly-spaced apertures is formed in second mounting member 173 to receive the ends of fiber-optic bundles 143A-143N. The rotable disc member 174 is mounted for rotation about its central axis and also includes a circular array of apertures.

Certain geometrical relationships are inherent in light-distributor device 124 of FIG. 8. First, the apertures in the arrays in the three members 172, 173 and 174 are all of substantially the same size. Further, the circular arrays of apertures in the three members all have substantially the same radius and, in each array, the apertures have the same regular spacing. Further, the circular arrays of apertures are all concentric about the same axial centerline. Still further, the mounting members 172 and 173 are positioned such that the arrays of apertures in members 172 and 173 ar in registration; as a consequence, the end of fiber-optic bundle 125 is directly opposed to the end of fiber-optic bundle 143A, the end of fiber-optic bundle 125B is directly opposed to the end of fiber-optic bundle 143B, and so forth.

Operation of the light-distributor 124 of FIG. 8 will now be explained. With lamp 161 energized, light is conveyed simultaneously through fiber-optic bundles 125A-125N to mounting member 172. Then, as member 174 is rotated, light is transmitted to optical fibers 143A-143N when, and only when, there is substantial registration between the apertures in the members 172, 173 and 174; otherwise, rotatable member 174 blocks the transmission of light. In the case where the apertures in rotatable member 174 are in registration with the apertures in members 172 and 173, parallel beams of light, all with the same phase, are transmitted simultaneously through fiber-optic bundles 143A-143N.

FIG. 9 shows a representative one of the transmitter stations which receives light from one of the fiber-optic bundles 153A-153N. The illustrated transmitter station, designated as station 153B, includes a mounting bracket 181 for supporting the ends of a bundle of optical fibers (i.e., bundle 143B), a focusing lens 183B to collimate light emitted from the bundle, and a mirror 185B for directing the collimated light onto the face of sheet 9. In the illustrated embodiment, mirror 185B is positioned at an angle of about forty-five degrees from horizontal to direct the collimated light generally perpendicularly onto sheet 9.

FIG. 9 also shows a representative one of the receiver stations which are stationarily mounted in alignment with respective ones of the transmitter stations. In FIG. 9, receiver station 190B is generally similar to transmitter station 153B and, as such, includes a mounting bracket 191B, a mirror 193B which is supported by the bracket at an appropriate angle for reflecting light which has been transmitted through sheet 9, and a focusing lens 195B mounted to focus the reflected light. A pair of bundles of optical fibers 197B and 198B are supported by bracket 191B to receive light from lens 195B.

FIG. 10 shows a light detector 201 for use with the system of FIGS. 7-9. In the illustrated embodiment, detector 201 includes an array of photoelectric detectors 203 arranged in two columns. The first column comprises detectors which detect light at the reference wavelength from respective ones of the fiber-optic bundles 197A-197N. The second column comprises detectors which detect light at the measurement wavelength from respective ones of the fiber-optic bundles 198A-198N.

Operation of the complete measurement system of FIGS. 7-10 will now be described. To initiate operation, lamp 161 is energized and conveys light to distributor 124 via fiber-optic bundles 125A-125N. The distributor 124 operates, as described above, to pass pulses of light simultaneously to fiber-optic bundles 143A-143N. The bundles 143A-143N carry the light to respective transmitter stations 153A-153N from which the light is directed onto the surface of sheet 9. The light which passes through the sheet is collected at receiver stations 190A-190N and then conveyed, via the pairs of fiber-optic bundles 197A-197N and 198A-198N, to detector 201. From the individual photoelectric transducers in detector 201, analog signals are electronically multiplexed and sent to an analog-to-digital converter and then to microprocessor-based computer 23A of FIG. 1. The computer then processes the signals to provide measurements of sheet properties at selected cross directional locations.

Although the present invention has been described with particular reference to the preferred embodiments, such disclosure should not be interpreted as limiting. Various other alterations and modifications will no doubt become apparent to those skilled in the art after having read the preceding disclosure. For example, it should be noted that if rotary multiplexor 27 of FIGURES and 5 is rotated sufficiently fast, modulating device 24 can be eliminated.

What is claimed is:

1. A system for detecting optically-sensitive properties of sheet materials during manufacture, comprising:
   a) a source of light;
   b) a first group of bundles of optical fibers, the first ends of the bundles being mounted to receive light from the source and the second ends of the bundles being mounted to direct the received light onto one face of a travelling sheet of material at generally regularly-spaced locations;

c) a second group of bundles of optical fibers, the first ends of the bundles of the second group being mounted at generally regularly-spaced locations to receive light which has been transmitted through the sheet material from corresponding ones of the optical fibers of the first group;

d) light detector means connected to the second ends of the optical fibers of the second group and mounted adjacent the same edge of the web of sheet material as the source of light;

e) the optical fibers of the first and second groups of bundles being of various lengths such that the light transmission paths through associated one of the fiber bundles in the first and second groups are not of constant length;

f) a first multiplexer for receiving light from said modulating means and for sequentially distributing the light to individual ones of the bundles of optical fibers in the first group, the first multiplexer including a light distributor means for conveying light simultaneously from the source to each of the bundles of optical fibers of the first group, g) the light distributor means comprising a first mounting member which receives the ends of a first set of the bundles of the first group of optical fibers in a first circular array, a second mounting member which receives the ends of a second set of the bundles of the first group of optical fibers in a second circular array, and a rotatable member disposed between the first and second mounting members, said rotatable member having a circular array of apertures formed therein for selectively blocking and unblocking optical communication between respective ones of the bundles of fibers in the first and second sets; and h) measurement means connected to the light detector means to provide measurements of optically sensitive properties of the sheet material based upon the detected light.

2. A system according to claim 1 wherein the optical fibers in the first and second groups of bundles are formed of quartz.

3. A system according to claim 1 further including a modulating means which is mounted for modulating light from the source before the light is transmitted through the first group of bundles of optical fibers.

4. A system according to claim 1 further including a demultiplexer for receiving light transmitted from individual ones of the bundles in the second group of optical fibers and for serially conveying the received light to the light detector means.

5. A system for detecting and measuring properties of sheet material which are sensitive to infrared light, comprising:

a) a plurality of light transmission stations mounted on a sheetmaking machine to extend in the cross direction at generally regular intervals for directing light onto the adjacent face of sheet material being produced;

b) first multiplexor means for providing a sequential series of light pulses;

c) a first group of bundles of optical fibers connected to convey light from the first multiplexor means to respective ones of the plurality of light transmission stations;

d) a plurality of light receiving stations mounted in alignment with corresponding ones of the light transmission stations for receiving light transmitted through the sheet material;

e) a second group of bundles of optical fibers connected to convey light from respective ones of the receiving stations, the optical fibers of the first and second groups of bundles having various lengths such that the light transmission paths through associated ones of the fiber bundles in the first and second groups are not of constant length;

f) a second multiplexor means for receiving light from the second group of bundles of optical fibers and for transmitting the light serially, the second multiplexor means including light distributor means having a first mounting member which receives the ends of a first set of the bundles of the first group of optical fibers in a first circular array, a second mounting member which receives the ends of a second set of the bundles of the first group of optical fibers in a second circular array, and a rotatable member disposed between the first and second mounting members, the rotatable member having a circular array of apertures formed therein for selectively blocking and unblocking optical communication between respective ones of the bundles of fibers in the first and second sets; and g) light detector means connected to the second multiplexor means for detecting the light intensity at particular bands of wavelengths at selected locations across the sheet material, the light detector means and the first multiplexor means being mounted adjacent the same edge of the sheet material being produced by the sheetmaking machine.

6. A system according to claim 5, further including modulating means which is mounted for modulating light from the source before the light is transmitted through the first group of bundles of optical fibers.

7. A system for detecting and measuring properties of sheet material which are sensitive to infrared light, comprising:

a) a plurality of light transmission stations mounted on a sheetmaking machine to extend in the cross direction at generally regular intervals for directing light onto the adjacent face of sheet material being produced;

b) a source of light;

c) a first group of bundles of optical fibers connected to convey light to respective ones of the plurality of light transmission stations;

d) light distributor means for conveying light simultaneously from the source to each of the bundles of optical fibers of the first group, the light distributor means having a first mounting member which receives the ends of a first set of the bundles of the first group of optical fibers in a first circular array, a second mounting member which receives the ends of a second set of the bundles of the first group of optical fibers in a second circular array, and a rotatable member disposed between the first and second mounting members, said rotatable member having a circular array of apertures formed therein for selectively blocking and unblocking optical communication between respective ones of the bundles of fibers in the first and second sets;

e) a plurality of light receiving stations mounted in alignment with corresponding ones of the light transmission stations for receiving light transmitted through the sheet material;

f) a second group of bundles of optical fibers connected to convey light from respective ones of the receiving stations;
g) a second multiplexor means for receiving light from the second group of bundles of optical fibers and for transmitting the light serially; and
h) light detector means connected to the second group of bundles of optical fibers for detecting the light intensity at particular bands of wavelengths at selected locations across the sheet material.

8. A system according to claim 7 wherein the optical fibers of the first and second groups of bundles have various lengths such that the light transmission paths through associated ones of the fiber bundles in the first and second groups are not of constant length.

* * * * *